United States Patent
Zhi et al.

(10) Patent No.: US 10,128,945 B2
(45) Date of Patent: Nov. 13, 2018

(54) MIMO VISIBLE LIGHT COMMUNICATION SYSTEM RECEIVING DEVICE

(71) Applicant: ZTE CORPORATION, Shenzhen, Guangdong Province (CN)

(72) Inventors: Zhou Zhi, Shenzhen (CN); Chao Xu, Shenzhen (CN); Tao Yang, Shenzhen (CN); Zhong Yu, Shenzhen (CN); Wei Wei, Shenzhen (CN)

(73) Assignee: ZTE CORPORATION (CN)

( * ) Notice: Subject to any disclaimer, the term of this patent is extended or adjusted under 35 U.S.C. 154(b) by 0 days.

(21) Appl. No.: 15/028,097

(22) PCT Filed: May 29, 2014

(86) PCT No.: PCT/CN2014/078724
§ 371 (c)(1),
(2) Date: Apr. 29, 2016

(87) PCT Pub. No.: WO2014/180412
PCT Pub. Date: Nov. 13, 2014

(65) Prior Publication Data
US 2016/0301470 A1 Oct. 13, 2016

(30) Foreign Application Priority Data
Oct. 8, 2013 (CN) .......................... 2013 1 0467767

(51) Int. Cl.
*H04B 10/00* (2013.01)
*G02B 3/00* (2006.01)
(Continued)

(52) U.S. Cl.
CPC .......... *H04B 10/116* (2013.01); *G02B 5/204* (2013.01); *G02B 27/0025* (2013.01);
(Continued)

(58) Field of Classification Search
CPC ....... G01N 33/48721; G01N 27/44704; G01N 27/44791; G01N 21/658; G01N 27/447;
(Continued)

(56) References Cited

U.S. PATENT DOCUMENTS 6,236,033 B1 * 5/2001 Ebbesen ................ B82Y 20/00
250/216
7,085,220 B2 * 8/2006 Fujikata ................ B82Y 10/00
369/112.27
(Continued)

FOREIGN PATENT DOCUMENTS

CN 1969206 A 5/2007
CN 101477044 A 7/2009
(Continued)

OTHER PUBLICATIONS

International Search Report and Written opinion dated Aug. 29, 2014 in PCT Patent Application No. PCT/CN2014/078724.
(Continued)

*Primary Examiner* — Ken N Vanderpuye
*Assistant Examiner* — Abbas H Alagheband
(74) *Attorney, Agent, or Firm* — Plumsea Law Group, LLC

(57) ABSTRACT

A receiving device for a multi-input multi-output (MIMO) visible light communication system includes a collimation unit, a metal thin film, a transparent substrate and a receiving unit. The receiving device performs receiving by using optical components, and uses the metal thin film as a main receiving component, which plays a role of filtering and enhanced transmission, and equals to implementing a function of filtering and signal amplification by using electronic components, but overcomes the nonlinear effect of the electronic components, thereby solving the problem of waveform distortion in receiving.

8 Claims, 2 Drawing Sheets

(51) Int. Cl.
| | |
|---|---|
| C02F 1/48 | (2006.01) |
| H01J 3/14 | (2006.01) |
| H04B 10/116 | (2013.01) |
| G02B 5/20 | (2006.01) |
| G02B 27/00 | (2006.01) |
| G02B 27/30 | (2006.01) |
| H04B 7/0413 | (2017.01) |
| H04B 10/69 | (2013.01) |
| G01N 21/25 | (2006.01) |
| G01N 27/447 | (2006.01) |
| G02B 5/18 | (2006.01) |
| G03B 27/32 | (2006.01) |
| G02B 27/46 | (2006.01) |

(52) U.S. Cl.
CPC ........... G02B 27/30 (2013.01); H04B 7/0413 (2013.01); H04B 10/697 (2013.01); *G01N 21/25* (2013.01); *G01N 27/447* (2013.01); *G02B 5/18* (2013.01); *G02B 27/46* (2013.01); *G03B 27/32* (2013.01)

(58) Field of Classification Search
CPC .. G01N 21/25; B82Y 15/00; C12Q 2525/185; G02B 27/30; G02B 27/46; G02B 5/204; G02B 27/0025; G02B 5/18; H04B 10/116; H04B 7/0413; H04B 10/697; C40B 60/12; G03B 27/32
USPC .......................................... 398/118; 359/569
See application file for complete search history.

(56) References Cited

U.S. PATENT DOCUMENTS

| | | | | |
|---|---|---|---|---|
| 7,501,289 | B2* | 3/2009 | Kubo ................... | G01N 21/553 422/82.11 |
| 7,692,795 | B2* | 4/2010 | Sasaki ................... | G06K 9/0004 356/445 |
| 9,257,661 | B2* | 2/2016 | Naya ................... | H01L 51/5012 |
| 2003/0185135 | A1* | 10/2003 | Fujikata ................. | B82Y 10/00 369/112.21 |
| 2003/0210469 | A1* | 11/2003 | Boege ................... | G01N 21/253 359/642 |
| 2005/0158850 | A1* | 7/2005 | Kubo ................... | G01N 21/553 435/287.2 |
| 2007/0036511 | A1* | 2/2007 | Lundquist ............. | G01J 3/2803 385/147 |
| 2007/0194357 | A1* | 8/2007 | Oohashi .......... | H01L 31/022408 257/292 |
| 2007/0222998 | A1* | 9/2007 | Sasaki ................... | G01N 21/553 356/445 |
| 2008/0252884 | A1* | 10/2008 | Carr ....................... | G01N 15/02 356/318 |
| 2009/0146081 | A1* | 6/2009 | Stark ....................... | B82Y 20/00 250/492.2 |
| 2009/0310133 | A1 | 12/2009 | Ogino et al. | |
| 2010/0059663 | A1 | 3/2010 | Desieres | |
| 2010/0075309 | A1* | 3/2010 | Maxham ............... | C12Q 1/6869 435/6.1 |
| 2010/0292101 | A1* | 11/2010 | So .......................... | C12Q 1/6869 506/16 |
| 2013/0032702 | A1* | 2/2013 | Le Perchec ............ | G02B 5/208 250/226 |
| 2013/0044299 | A1* | 2/2013 | Xie ....................... | G02B 5/1876 355/18 |
| 2013/0308102 | A1* | 11/2013 | Natsumeda ............ | G03B 21/14 353/20 |
| 2014/0087474 | A1* | 3/2014 | Huber .................. | C12Q 1/6869 436/94 |
| 2014/0110259 | A1* | 4/2014 | Takahashi ........ | G01N 33/48721 204/452 |
| 2016/0289669 | A1* | 10/2016 | Fan ....................... | C12Q 1/6874 |

FOREIGN PATENT DOCUMENTS

| | | |
|---|---|---|
| CN | 101672941 A | 3/2010 |
| CN | 101887142 A | 11/2010 |
| CN | 102667546 A | 9/2012 |
| CN | 102736154 A | 10/2012 |
| JP | 2004363756 A | 12/2004 |
| JP | 2010160212 A | 7/2010 |
| JP | 2012235411 A | 11/2012 |
| JP | WO 2014087927 A1 * 6/2014 ............. G02B 5/008 |  |

OTHER PUBLICATIONS

Office Action dated Apr. 25, 2017 for Japanese Patent Application No. 2016-521272.

Office Action dated Nov. 3, 2017 for Chinese application No. 201310467767.0.

* cited by examiner

MIMO VISIBLE LIGHT COMMUNICATION SYSTEM RECEIVING DEVICE

CROSS-REFERENCE TO RELATED APPLICATION(S)

This application is the U.S. National Phase application of PCT application number PCT/CN2014/078724 having a PCT filing date of May 29, 2014, which claims priority of Chinese patent application 201310467767.0 filed on Oct. 8, 2013, the disclosures of which are hereby incorporated by reference.

TECHNICAL FIELD

The present document relates to the field of visible light communication technology, and particularly, to a receiving device for a multi-input multi-output (MIMO) visible light communication system.

BACKGROUND OF RELATED ART

The visible light communication is a wireless communication technique, and it utilizes the visible light with frequency between 390 THz and 857 THz as the communication medium to accomplish information transfer.

In order to improve the communication capacity, the frequency division multiplexing technology or wavelength-division multiplexing technology is widely used in either wireless communication or optical fiber communication. Compared with the communication of single frequency, signals are transmitted with multiple frequencies in the frequency division multiplexing technology. The electromagnetic wave of each frequency can serve as an independent signal carrier to transmit different signals respectively, thereby greatly improving the communication capacity. However, a receiving end of the wireless frequency division multiplexing needs to be configured with antennas to receive electromagnetic wave signals and convert electromagnetic waves into electrical signals, thus the effect of information receiving has a lot to do with the antenna performance and antenna position.

At present, a large number of electronic parts and components are used in the MIMO visible light communication system, due to causes such as nonlinearity existing within the channels, inter-path interference and waveform distortion are easily generated.

SUMMARY

The object of the embodiments of the present document is to put forward a receiving device for a MIMO visible light communication system, to solve the problem of waveform distortion in receiving.

In order to solve the above technical problem, the following technical scheme is adopted;

a receiving device for a multi-input multi-output (MIMO) visible light communication system comprises a collimation unit, a metal thin film, a transparent substrate and a receiving unit; wherein, the collimation unit is configured to: receive incident light, and collimate the incident light, and obtain the collimated light, to make the collimated light output vertically incident to the metal thin film;

the metal thin film is configured to: receive the collimated light, filter the collimated light, obtain the filtered light, and output the filtered light to the transparent substrate;

the transparent substrate is configured to: transmit the filtered light; and the receiving unit is configured to: receive the light transmitted by the transparent substrate.

Alternatively, the collimation unit comprises a convergence lens, a field stop and a collimation lens; wherein, the convergence lens is configured to: receive the incident light, converge the incident light to a focal plane, and obtain the converged light;

the collimation lens is configured to: receive the converged light, and turn the converged light into parallel light; and the field stop is located between the convergence lens and the collimation lens, and located on the focal plane of the convergence lens, and is configured to: limit a field of view of the incident light, to make the parallel light output as the collimated light vertically incident to the metal thin film.

Alternatively, a two-dimensional array of nanopores is distributed on the metal thin film, and a distance between any two points on the nanopore is less than a wavelength of the incident light.

Alternatively, shapes of the nanopores are squares, or circles, or triangles.

Alternatively, the metal thin film comprises N zones, shapes of nanopores in different zones are different, or areas of nanopores in different zones are different, or periods of nanopores in different zones are different.

Alternatively, in the N zones, shapes of nanopores within a same zone are all identical, areas of nanopores within a same zone are all identical, and periods of nanopores within a same zone are all identical.

Alternatively, material of the metal thin film is gold, or silver.

Alternatively, the receiving unit is a two-dimensional charge coupled device (CCD) array or a two-dimensional complementary metal-oxide semiconductor (CMOS) array, each CCD or CMOS pixel corresponds to one nanopore.

In the embodiment of the present document, the receiving device put forward based on the surface plasmons performs receiving by using optical components, and uses the metal thin film as a main receiving component, which plays a role of filtering and enhanced transmission, and equals to implementing a function of filtering and signal amplification by using electronic components, but overcomes the nonlinear effect of the electronic components, thereby solving the problem of waveform distortion in receiving.

The pixel level in the receiving device of the embodiment of the present document is at the nanometer level, thus the receiving device has an advantage of small volume, and the frequency for receiving the light waves is mainly decided by detecting components, and the detection range of the detecting components such as the CCD and CMOS has covered the entire visible light waveband at present, therefore, the receiving device of the embodiment of the present document implements receiving of broadband signals.

BRIEF DESCRIPTION OF THE DRAWINGS

The accompanying drawings in the embodiments of the present document will be described below, the accompanying drawings in the embodiments are used to provide a further understanding of the present document, and explain the present document together with the specifications, but do not constitute a limitation on the protection scope of the present document.

Figure 1:
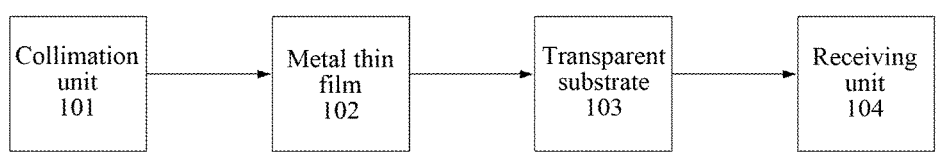
FIG. 1 is a diagram of a composition structure of the receiving device of the embodiment of the present document.

In the drawings, 1011 is a convergence lens, 1012 is a field stop, 1013 is a collimation lens, 102 is a metal thin film, 103 is a transparent substrate, 104 is a receiving unit, and 301 is a nanopore.

PREFERRED EMBODIMENTS

For the people skilled in the art to understand easily, the present document will be further described in combination with the accompanying drawings, which cannot be used to limit the protection scope of the embodiments of the present document.

FIG. 1 is a diagram of a composition structure of the receiving device of the embodiment of the present document, as shown in FIG. 1, a receiving device for a MIMO visible light communication system of the embodiment of the present document includes a collimation unit 101, a metal thin film 102, a transparent substrate 103 and a receiving unit 104; wherein, the collimation unit 101 is configured to: receive incident light, and collimate the incident light, to make the collimated light output vertically incident to the metal thin film;

the metal thin film 102 is configured to: receive the collimated light, filter the collimated light, and output the filtered light to the transparent substrate 103;

the transparent substrate 103 is configured to: transmit the filtered light; and the receiving unit 104 is configured to: receive the light transmitted by the transparent substrate.

In the embodiment of the present document, filtering the collimated light by using the metal thin film is based on the existence of Extraordinary Optical Transmission (EOT) phenomenon, discovered in the experiment and reported by Ebbesen et al. for the first time in 1998 when the light wave passes through the punched silver thin film. Ebbesen et al. punched a two-dimensional periodic sub-wavelength circular hole array on a silver thin film with the quartz as a substrate, when an aperture does not exceed a half of the incident wavelength, the light transmission enhancement characteristic will show within specific wavelengths, that is, there are two important optical characteristics: "transmission enhancement" and "filtering", which challenges the classical diffraction optics theory. Ebbesen explains such strange local transmission enhancement phenomenon as the Surface Plamons (SPs) effect, that is, resonance excitation and coupling of the Surface Plasmon Polaritions (SPPs) of the metal film leads to such enhancement effect, and a light wave transmitted in the metal is called a Surface Plasmon Wave (SPW). Nowadays, with the development of the Surface Plasmon Resonance (SPR) technology, the SPR technology has become an indispensable part in the fields of environmental monitoring, analytical biochemistry, drug research and development and food supervision.

Figure 2:
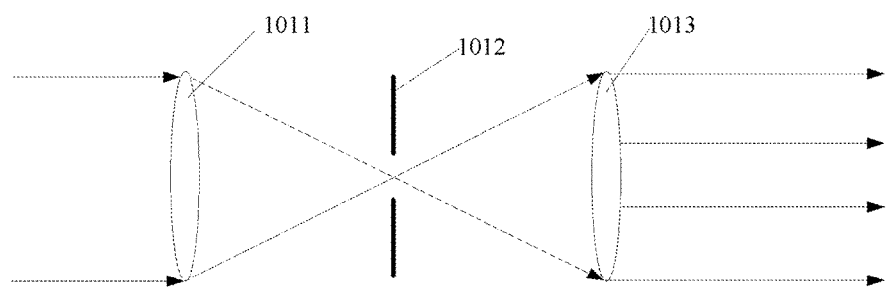
FIG. 2 is a diagram of a composition structure of a collimation unit in the receiving device of the embodiment of the present document.

FIG. 2 is a diagram of a composition structure of a collimation unit 101 in the receiving device of the embodiment of the present document, and as shown in FIG. 2, the collimation unit 101 includes a convergence lens 1011, a field stop 1012 and a collimation lens 1013; wherein, the convergence lens 1011 is configured to: receive the incident light, and converge the incident light to a focal plane;

the collimation lens 1013 is configured to: receive the converged light, and turn the converged light into parallel light; and the field stop 1012 is located between the convergence lens and the collimation lens, and located on the focal plane of the convergence lens, and is configured to: limit a field of view of the incident light, to make the output parallel light vertically incident to the metal thin film.

The periodically arranged two-dimensional array of nanopores is distributed on the metal thin film, and the size of the nanopore satisfies that a distance between any two points on the nanopore is less than a wavelength of the incident light.

Figure 3:
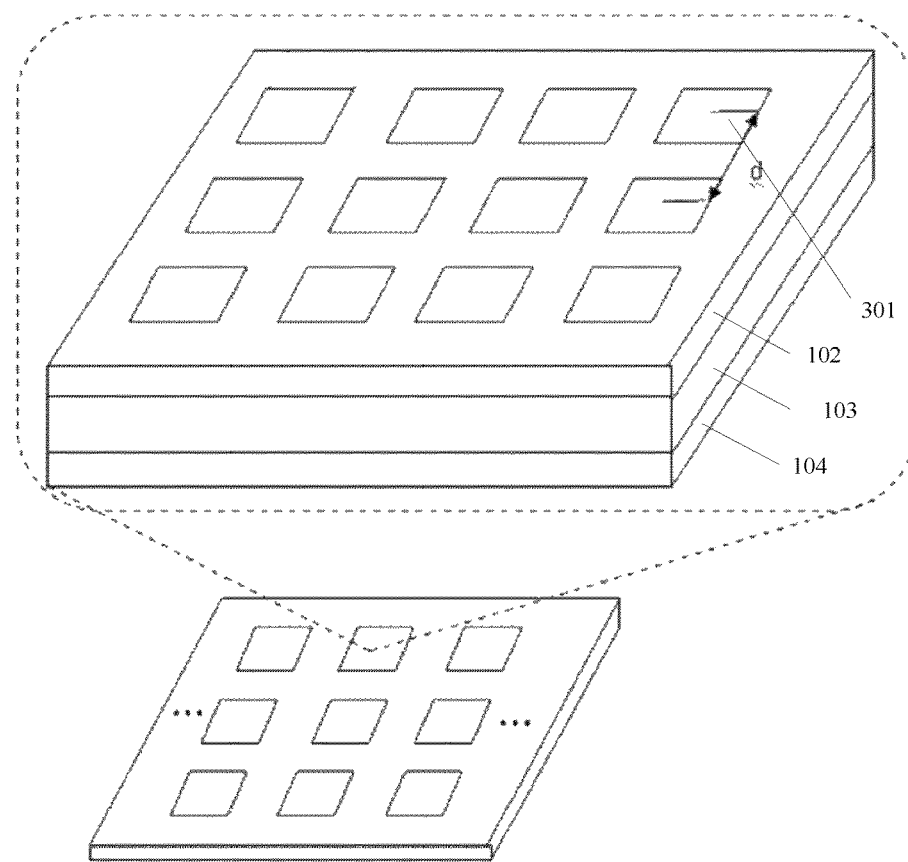
FIG. 3 is a schematic diagram of a two-dimensional array of square nanopores in the embodiment of the present document.

The nanopores may be in any shapes, such as squares (see FIG. 3), or circles, or triangles.

The reason why the periodical two-dimensional array of the nanopores has the enhanced transmission is the existence of resonance and excitation of the SPPs. The SPPs resonance is first put forward by Ebbesen et al. and accepted by the majority of people, the physical image thereof is that incident electromagnetic waves and surface free electrons of the punched metal thin film motivate the surface SPPs through the momentum compensation provided by the reciprocal lattice vectors of the pore array, and these SPPs constrained on the metal surface pass through the pore tunnels to the other end of the metal thin film, and then radiate the electromagnetic waves through an inverse process, thereby implementing sub-wavelength transmission of the electromagnetic waves. Based on the mechanism, different arrangement ways of the nanopores on the metal thin film will correspond to different reciprocal lattice vectors, thus the arrangement ways of the nanopores directly decide the resonance peak positions of the SPPs.

For example, when the shapes of the nanopores are squares, in the case that the incident light is vertically incident, the wavelength of the transmission peak thereof is approximate to:

$$\lambda_{max} = \frac{d}{\sqrt{i^2 + j^2}} \sqrt{\frac{\varepsilon_m \varepsilon_d}{\varepsilon_m + \varepsilon_d}}$$

wherein, i and j are reciprocal lattice vectors corresponding to different orders, d is a period of the two-dimensional array of the nanopores, $\varepsilon_m$ is a dielectric constant of the metal thin film, and $\varepsilon_d$ is a dielectric constant of the medium in contact with the upper surface of the metal thin film.

When the shapes of the nanopores are triangles, in the case that the incident light is vertically incident, the wavelength of the transmission peak thereof is approximate to:

$$\lambda_{max} = \frac{d}{\frac{4}{3}\sqrt{i^2 + ij + j^2}} \sqrt{\frac{\varepsilon_m \varepsilon_d}{\varepsilon_m + \varepsilon_d}}$$

In order to better understand the working mechanism of the SPPs enhanced transmission, it is to understand by borrowing the equation put forward by Degiron A et al., and the equation is:

$$I_{cie}(\lambda, h) = f_{ci}(\lambda) T(\lambda, h) f_{ce}(\lambda)$$

wherein, h is the thickness of the metal thin film, $\lambda$, is the wavelength, $I_{cie}(\lambda, h)$ is the transmission intensity when the light passes through the periodic two-dimensional array of nanopores, $f_{ci}(\lambda)$ is a coupling function of the upper surface of the metal thin film, $f_{ce}(\lambda)$ is a coupling function of the lower surface of the metal thin film, and $T(\lambda, h)$ is an intermediate truncation function of passing through the nanopores.

In the three factors affecting the transmission intensity of the output light, $f_{ci}(\lambda)$ and $f_{ce}(\lambda)$ are mainly related to geometric parameters of the surface appearance of the metal thin film, such as the period of the two-dimensional array of nanopores and the depth of the nanopore and so on; and the $T(\lambda, h)$ is mainly related to shape features of the nanopores.

In order to receive light waves of different frequencies, the two-dimensional array of nanopores on the metal thin film can be divided into a plurality of zones, each zone can contain several thousand to tens of thousands of nanopores, shapes of the nanopores in the array of nanopores in different zones are different, or areas thereof are different, or periods thereof are different; and within the same zone scope, shapes of the nanopores in the array of nanopores are all identical, areas thereof are all identical and periods thereof are all identical.

The material of the metal thin film must satisfy that the plasma frequency thereof is greater than the frequency of the incident light, because only in this way, the incident light may form surface plasma waves on the surface of the metal thin film, for example, the gold or silver plasma frequency is at the ultraviolet band, then when the visible light is incident, the surface plasma waves may be formed on the surface of the metal thin film, and properties of the gold and silver are relatively more stable, and they are not easy to be oxidized, thus the material of the metal thin film being gold or silver is a preferred scheme of the present document.

Changing the nanopore shape or area of the two-dimensional array of nanopores may change the wavelength of the transmission peak. For example, when the metal thin film is made of silver, the thickness is 320 nanometers (nm), and the array of nanopores is composed of square nanopores with side length of 320 nm and period of 750 nm, the wavelength of the transmission peak is 800 nm; if the material, thickness of the metal thin film, nanopore shape and period of the two-dimensional array of nanopores are not changed, but the side length of the nanopores is changed to 248 nm, the wavelength of the transmission peak is 780 nm; and when the array of nanopores is changed to be made up of circular pores with diameter of 280 nm, the wavelength of the transmission peak is 750 nm.

Similarly, changing the period of the two-dimensional array of nanopores may also change the wavelength of the transmission peak. For example, when the two-dimensional array of nanopores is made up of circular nanopores with period of 500 nm and diameter of 250 nm, the wavelength of the transmission peak is 630 nm; when the period is 600 nm and the other parameters are all identical, the wavelength of the transmission peak is 710 nm.

The transparent substrate is made of transparent materials, the material of the transparent substrate is not limited in the embodiments of the present document, and materials with better transmission of light will all be ok, such as polymers PMMA or $SiO_2$.

The receiving unit may be implemented by using a two-dimensional CCD array or a two-dimensional CMOS array, each CCD or CMOS pixel corresponds to one nanopore.

Figure 4:
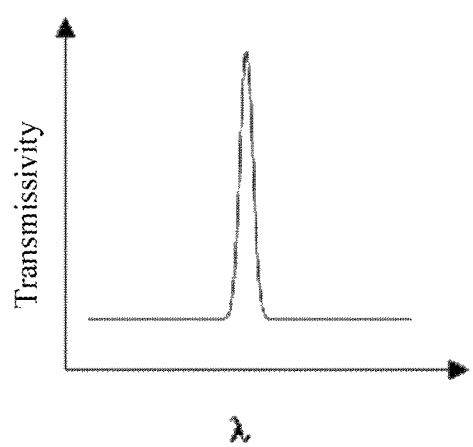
FIG. 4 is a transmission spectrum chart of the metal thin film in the embodiment of the present document.

FIG. 4 is a transmission spectrum chart of the metal thin film, and as shown in FIG. 4, a horizontal ordinate represents the wavelength and a vertical ordinate represents the light-wave transmissivity in FIG. 4. When the optical signals pass through the two-dimensional array of nanopores of the metal thin film, only the optical signals within a specific frequency range are transmitted, and the optical signals outside the frequency range are interdicted, eventually the optical signals of different frequencies are received in the receiving unit, and through the continuous and fast measurement of the receiving unit, the signal size of the light at each moment can be obtained, and the receiving unit converts the detected optical signals of various frequencies into electrical signals, distributes the signals to various subchannels to transmit, and performs demodulation with the demodulator, thereby obtaining the original transmitted signals.

In the embodiment of the present document, the receiving device put forward based on the surface plasmons performs receiving by using optical components, and uses the metal thin film as a main receiving component, which plays a role of filtering and enhanced transmission, and equals to implementing a function of filtering and signal amplification by using electronic components, but overcomes the nonlinear effect of the electronic components, thereby solving the problem of waveform distortion in receiving.

The pixel level in the receiving device of the embodiment of the present document is at the nanometer level, thus the receiving device has an advantage of small volume, and the frequency for receiving the light waves is mainly decided by detecting components, and the detection range of the detecting components such as the CCD and CMOS has covered the entire visible light waveband at present, therefore, the receiving device of the embodiment of the present document can implement receiving of broadband signals.

It should be noted that the above embodiments are only for the people skilled in the art to understand easily, and are not used to limit the protection scope of the present document, and in the premise of not departing from the inventive concept of the present document, all apparent substitutions and improvements of the present document made by the people skilled in the art are within the protection scope of the present document.

INDUSTRIAL APPLICABILITY

In the embodiment of the present document, the receiving device put forward based on the surface plasmons performs receiving by using optical components, and uses the metal thin film as a main receiving component, which plays a role of filtering and enhanced transmission, and equals to implementing a function of filtering and signal amplification by using electronic components, but overcomes the nonlinear effect of the electronic components, thereby solving the problem of waveform distortion in receiving. The pixel level in the receiving device of the embodiment of the present document is at the nanometer level, thus the receiving device has an advantage of small volume, and the frequency for receiving the light waves is mainly decided by detecting components, and the detection range of the detecting components such as the CCD and CMOS has covered the entire visible light waveband at present, therefore, the receiving device of the embodiment of the present document implements receiving of broadband signals. Therefore, the present document has a very strong industrial applicability.

What is claimed is:

1. A receiving device for a multi-input multi-output (MIMO) visible light communication system, comprising a collimation unit, a metal thin film, a transparent substrate and a receiving unit; wherein, the collimation unit is configured to: receive incident light, and collimate the incident light, and obtain the collimated light, to make the collimated light output vertically incident to the metal thin film;

the metal thin film is configured to: receive the collimated light, filter the collimated light, obtain the filtered light, and output the filtered light to the transparent substrate;

the transparent substrate is configured to: transmit the filtered light; and the receiving unit is configured to: receive the light transmitted by the transparent substrate;

wherein plasma frequency of the metal thin film is greater than frequency of the light;

wherein a two-dimensional array of nanopores is distributed on the metal thin film, and a distance between any two points on the nanopore is less than a wavelength of the incident light;

wherein the receiving unit is a two-dimensional charge coupled device (CCD) array or a two-dimensional complementary metal-oxide semiconductor (CMOS) array, each CCD or CMOS pixel corresponds to one nanopore.

2. The receiving device according to claim 1, wherein, the collimation unit comprises a convergence lens, a field stop and a collimation lens; wherein, the convergence lens is configured to: receive the incident light, converge the incident light to a focal plane, and obtain the converged light;

the collimation lens is configured to: receive the converged light, and turn the converged light into parallel light; and the field stop is located between the convergence lens and the collimation lens, and located on the focal plane of the convergence lens, and is configured to: limit a field of view of the incident light, to make the parallel light output as the collimated light vertically incident to the metal thin film.

3. The receiving device according to claim 1, wherein, shapes of the nanopores are squares, or circles, or triangles.

4. The receiving device according to claim 1, wherein, the metal thin film comprises N zones, shapes of nanopores in different zones are different, or areas of nanopores in different zones are different, or periods of nanopores in different zones are different.

5. The receiving device according to claim 4, wherein, in the N zones, shapes of nanopores within a same zone are all identical, areas of nanopores within a same zone are all identical, and periods of nanopores within a same zone are all identical.

6. The receiving device according to claim 1, wherein, material of the metal thin film is gold, or silver.

7. The receiving device according to claim 1, wherein, when shapes of the nanopores are squares, and the light is vertically incident, wavelength of a transmission peak of the light is:

$$\lambda_{max} = \frac{d}{\sqrt{i^2+j^2}}\sqrt{\frac{\varepsilon_m \varepsilon_d}{\varepsilon_m + \varepsilon_d}}$$

wherein, i and j are reciprocal lattice vectors corresponding to different orders, d is a period of two-dimensional array of the nanopores, $\varepsilon_m$ is a dielectric constant of the metal thin film, and $\varepsilon_d$ is a dielectric constant of medium in contact with the upper surface of the metal thin film.

8. The receiving device according to claim 1, wherein, when shapes of the nanopores are triangles, and the light is vertically incident, wavelength of a transmission peak of the light is:

$$\lambda_{max} = \frac{d}{\frac{4}{3}\sqrt{i^2+ij+j^2}}\sqrt{\frac{\varepsilon_m \varepsilon_d}{\varepsilon_m + \varepsilon_d}}$$

wherein, i and j are reciprocal lattice vectors corresponding to different orders, d is a period of two-dimensional array of the nanopores, $\varepsilon_m$ is a dielectric constant of the metal thin film, and $\varepsilon_d$ is a dielectric constant of medium in contact with the upper surface of the metal thin film.

* * * * *